US00PP21576P2

(12) United States Plant Patent
Egger

(10) Patent No.: US PP21,576 P2
(45) Date of Patent: Dec. 14, 2010

(54) ***HEUCHERA* PLANT NAMED 'MYSTERIA'**

(50) Latin Name: ***Heuchera* hybrid**
Varietal Denomination: Mysteria

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/658,176

(22) Filed: Feb. 3, 2010

(51) Int. Cl.
*A01H 5/00* (2006.01)

(52) U.S. Cl. ..... Plt./440

(58) Field of Classification Search ..... Plt./440
See application file for complete search history.

*Primary Examiner*—Kent L Bell
(74) *Attorney, Agent, or Firm*—Klarquist Sparkman, LLP

(57) ABSTRACT

A new and distinct hybrid of *Heuchera* plant characterized by very free flowering and with a long bloom time (bloom from early spring to late fall in Canby, Oreg.), excellent warm pink flowers in dense clusters that fade to darker pink, leaf color pewter with dark veins, excellent tolerance to heat and humidity, and excellent vigor.

1 Drawing Sheet

Botanical denomination: *Heuchera* hybrid.
Variety designation: 'Mysteria'.

BACKGROUND OF THE INVENTION

The present invention relates to a new and distinct cultivar of *Heuchera* and given the cultivar name of 'Mysteria'. *Heuchera* is in the family *Saxifragaceae. Heuchera* 'Mysteria' originated from a cross between *Heuchera* 'Lipstick' (U.S. Plant patent application No. 12/800,260) as the seed parent, and *Heuchera* 831-2, a proprietary non-commercial hybrid as the pollen parent *Heuchera* 831-2 has *Heuchera villosa* var. *macrorhiza* as the pollen parent. This breeding plan was to produce a hybrid with a long bloom time, heat and humidity tolerance, and quality large flowers on short stems.

Compared to the seed parent, *Heuchera* 'Lipstick', the new cultivar has a larger leaf size of pewter leaves rather than green and warm pink rather than red flowers.

Compared to the pollen parent, *Heuchera* 827-1, the new cultivar has silver rather than purple leaves and warm pink rather than white and pink flowers.

Compared to *Heuchera* 'Milan' (U.S. Plant patent application No. 12/658,174), the new cultivar is a larger plant and has larger, lighter colored leaves and darker pink flowers.

Compared to *Heuchera* 'Raspberry Ice' (U.S. Plant Pat. No. 13,340), the new cultivar has darker foliage with more silver, larger, more numerous flowers, and a longer bloom time.

This new *Heuchera* is uniquely distinguished by:

1. very free flowering and with a long bloom time (bloom from early spring to late fall in Canby, Oreg.),
2. excellent warm pink flowers in dense clusters that fade to darker pink,
3. leaf color pewter with dark veins,
4. excellent tolerance to heat and humidity,
5. excellent vigor.

This new cultivar has been reproduced only by asexual propagation (tip cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The photo shows a 1 year-old plant of *Heuchera* 'Mysteria' growing in the ground in full sun in the garden in August in Canby, Oreg.

DETAILED PLANT DESCRIPTION

The following is a detailed description of the new *Heuchera* cultivar based on observations taken in May of one-year-old specimens growing in the ground in the garden in full sun in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—33 cm tall from top of the foliage to the ground and 43 cm wide.
*Habit.*—Mounding.
*Vigor.*—Excellent.

Leaf:

*Type.*—Simple.
*Arrangement.*—Rosette.
*Shape.*—Broadly ovate.
*Lobing/division.*—5 main lobes, the terminal is the longest; shallow secondary lobes.
*Venation.*—Palmate.
*Margins.*—Broadly crenate and somewhat undulate.
*Apex.*—Mucronulate.

*Base.*—Cordate, lobes strongly overlapping at the base.
*Blade size.*—Grows to 13 cm long and 11.5 cm wide.
*Texture.*—Leathery.
*Surface texture.*—Glandular on the both sides.
*Petiole description.*—Grows to 18.5 cm long and 3 mm wide, glandular hairs, closest to Greyed Purple N186C.
*Leaf color.*—Topside, spring leaves are silver purple with dark veins and margins, Purple N77C and N77C with veins and margins N187A, bottom side Greyed Purple 187B; mature summer thru winter leaves are silver, Black 202C with dark veins and margins, between Greyed Green N189A and Black 202A, bottom side Greyed Purple 187B.

Inflorescence:
*Size.*—Grows to 8.5 cm wide and 18 cm long.
*Type.*—Thyrse.
*Number of flowers per thyrse.*—About 190.
*Number of thyrse.*—About 30 for the whole flowering season.
*Size of inflorescence.*—Grows to 16 cm long and 6 cm wide.
*Peduncle.*—About 44 cm long, 3 mm wide at base, Greyed Purple N186C, glandular hairs, with no cauline leaves.
*Pedicel.*—Variable in size, with glandular hairs, Greyed Purple N186C.
*Bloom period.*—May through November in Canby, Oreg.

Flower bud:
*Size.*—3 mm wide and 5 mm long.
*Description.*—Glandular puberulent, ovoid, down facing.
*Color.*—Red 54A.

Flower:
*Type.*—Perfect.
*Shape.*—Campanulate.
*Size.*—7 mm long and 6.5 mm wide.
*Corolla description.*—5 in number, inconspicuous, 2.5 mm long and 1 mm wide, spatulate, tip acute, margin entire, glabrous on top and glandular on bottom, Red 55D.
*Calyx description.*—Campanulate, 7 mm long and 6.5 mm wide, with 5 lobes divided ⅓ way to the base, each 2 mm wide and 2.5 mm long, glandular hairs outside and inside, tips acute, margin entire; inside color Red 54A, outside Red 55B with bottom ⅓, Red 54A, and lobe tips Red 53A.
*Stamen description.*—5 in number, filaments 1.5 mm long, White NN155C, anthers sterile, 0.5 mm, Red Purple 71A.
*Pistil description.*—1, 2-beaked, 4 mm long; ovary 1 mm long, Yellow 1D; style 2 mm long, Yellow 12D, stigma White 155A.
*Fragrance.*—None.
*Lastingness.*—Each thyrse blooms for about 3 weeks on the plant.

Fruit: none produced.
Seed: none.
Pest and Disease Tolerance: Excellent disease resistance to powdery mildew, the common problem of *Heuchera.* Susceptible to *Heuchera* rust and root weevils.

I claim:

1. A new and distinct *Heuchera* plant as herein illustrated and described.

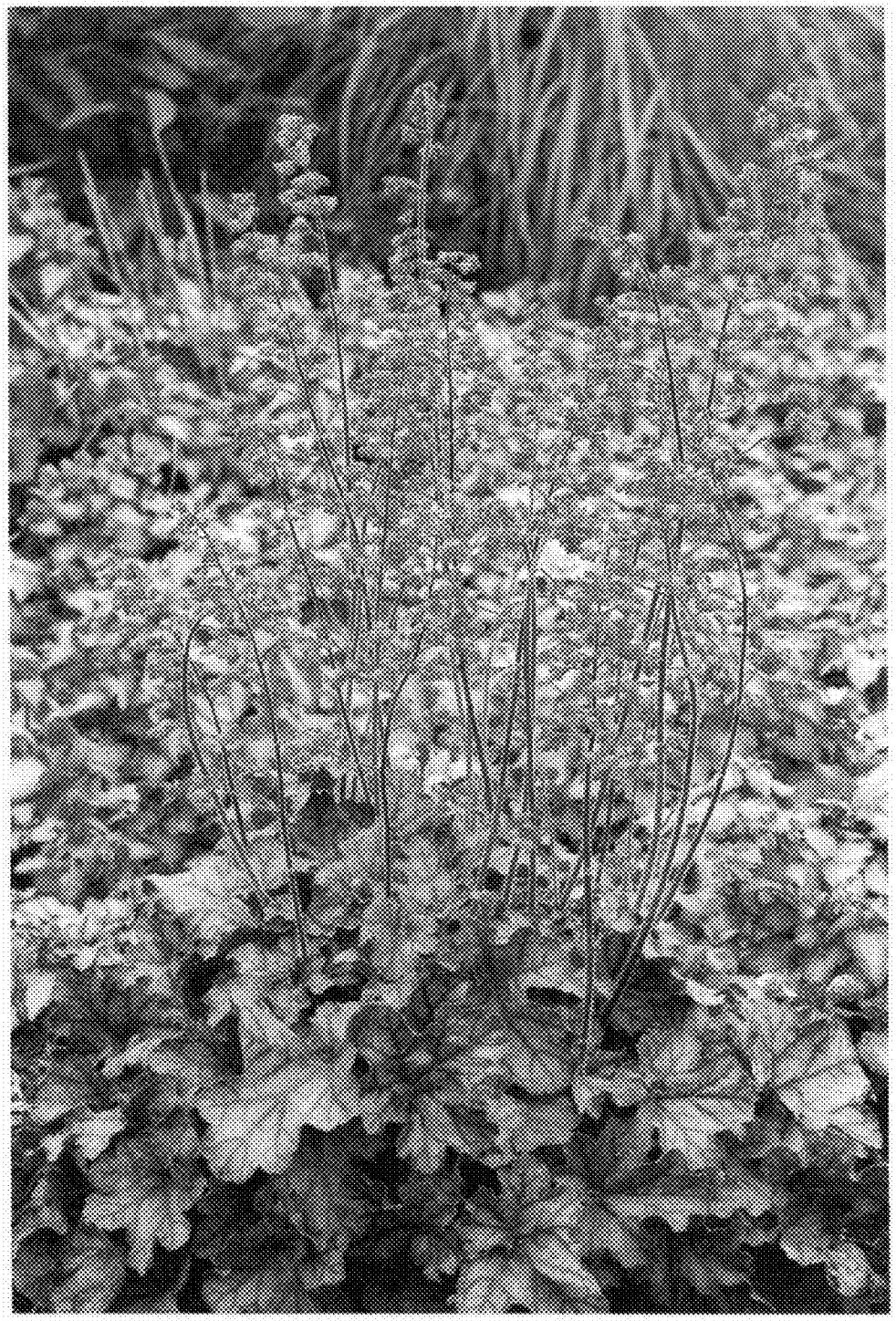

* * * * *